United States Patent [19]

Wilmot

[11] Patent Number: 5,295,965
[45] Date of Patent: Mar. 22, 1994

[54] AUTOMATIC INJECTORS

[75] Inventor: John G. Wilmot, Kent, England

[73] Assignee: Survival Technology, Inc., Rockville, Md.

[21] Appl. No.: 936,236

[22] Filed: Aug. 26, 1992

[30] Foreign Application Priority Data

Jan. 7, 1992 [GB] United Kingdom ............ 9200219

[51] Int. Cl.$^5$ ............................................. A61M 5/00
[52] U.S. Cl. ........................................ 604/136; 604/218
[58] Field of Search ............ 604/218, 187, 134, 135, 604/136, 137

[56] References Cited

U.S. PATENT DOCUMENTS

| | | | |
|---|---|---|---|
| 2,674,246 | 4/1954 | Bower. | |
| 2,752,918 | 7/1956 | Uytenbogaart. | |
| 3,797,489 | 3/1974 | Sarnoff | 604/136 |
| 3,880,163 | 4/1975 | Ritterskamp | 604/136 |
| 3,941,130 | 3/1976 | Tibbs | 604/136 |
| 4,664,654 | 5/1987 | Strauss. | |
| 4,767,413 | 8/1988 | Haber. | |
| 4,813,426 | 3/1989 | Haber. | |
| 5,114,406 | 5/1992 | Gabriel et al. | 604/136 |

FOREIGN PATENT DOCUMENTS

| | | |
|---|---|---|
| 0361668 | 4/1990 | European Pat. Off. . |
| 0416353 | 3/1991 | European Pat. Off. . |
| 2019296 | 11/1971 | Fed. Rep. of Germany . |
| 2650187 | 2/1991 | France . |
| 8800066 | 1/1988 | PCT Int'l Appl. . |
| 8912473 | 12/1989 | PCT Int'l Appl. . |
| 9101153 | 2/1991 | PCT Int'l Appl. . |
| 728248 | 4/1955 | United Kingdom . |

Primary Examiner—John D. Yasko
Attorney, Agent, or Firm—Cushman, Darby & Cushman

[57] ABSTRACT

An automatic injector having a needle which is driven out of a body of the injector automatically by drive means also has an associated protective, or sharps, assembly. The sharps assembly has a cover member adapted to cover the needle after the injector has been used. The assembly is operative to provide relative movement between the injection needle and the cover member after injection so that the cover member covers the needle after use. The cover member is preferably actuated automatically so that the user never sees the needle.

21 Claims, 10 Drawing Sheets

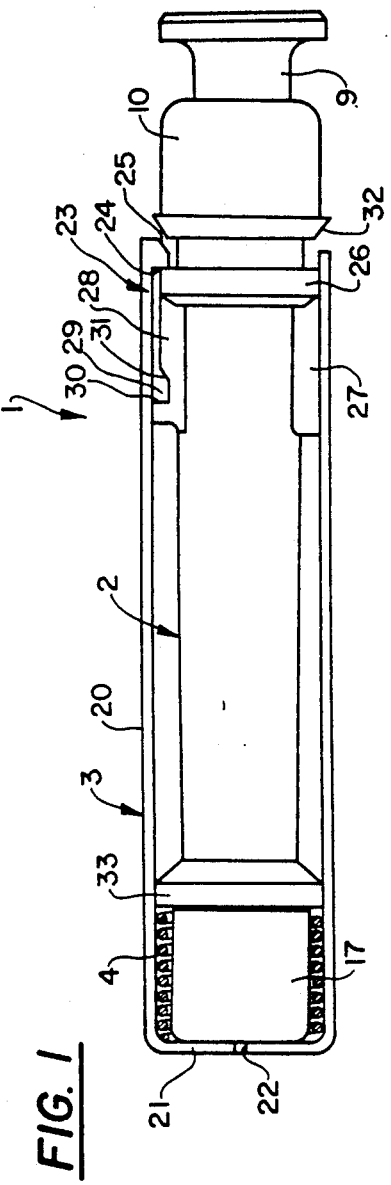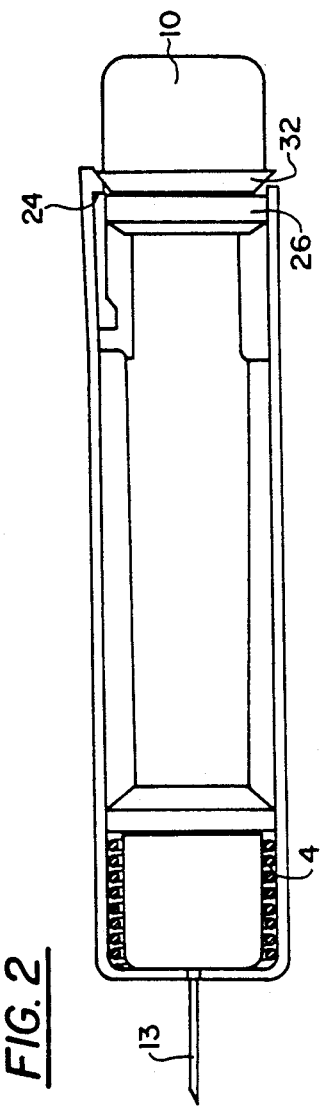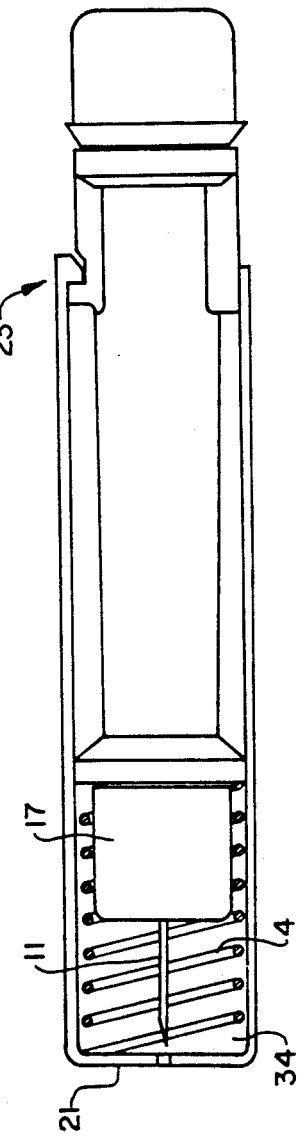

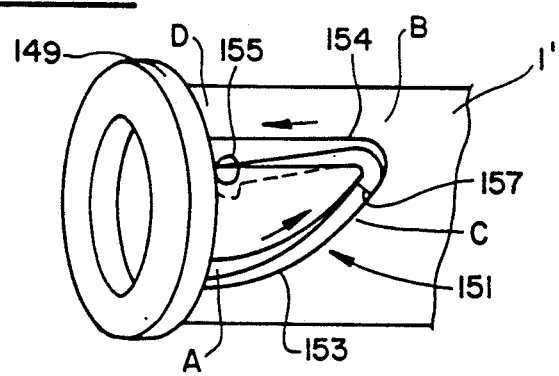
FIG. 17
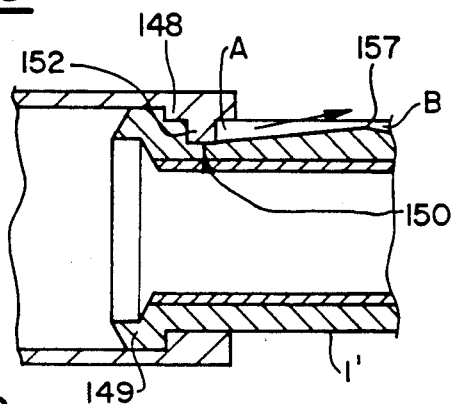
FIG. 18
FIG. 19
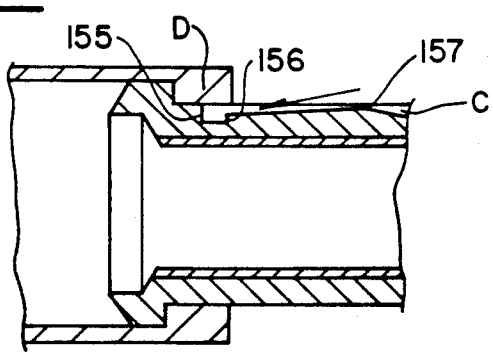
FIG. 23
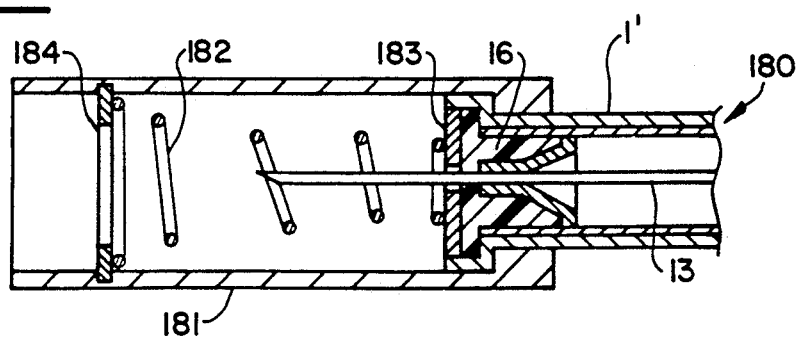

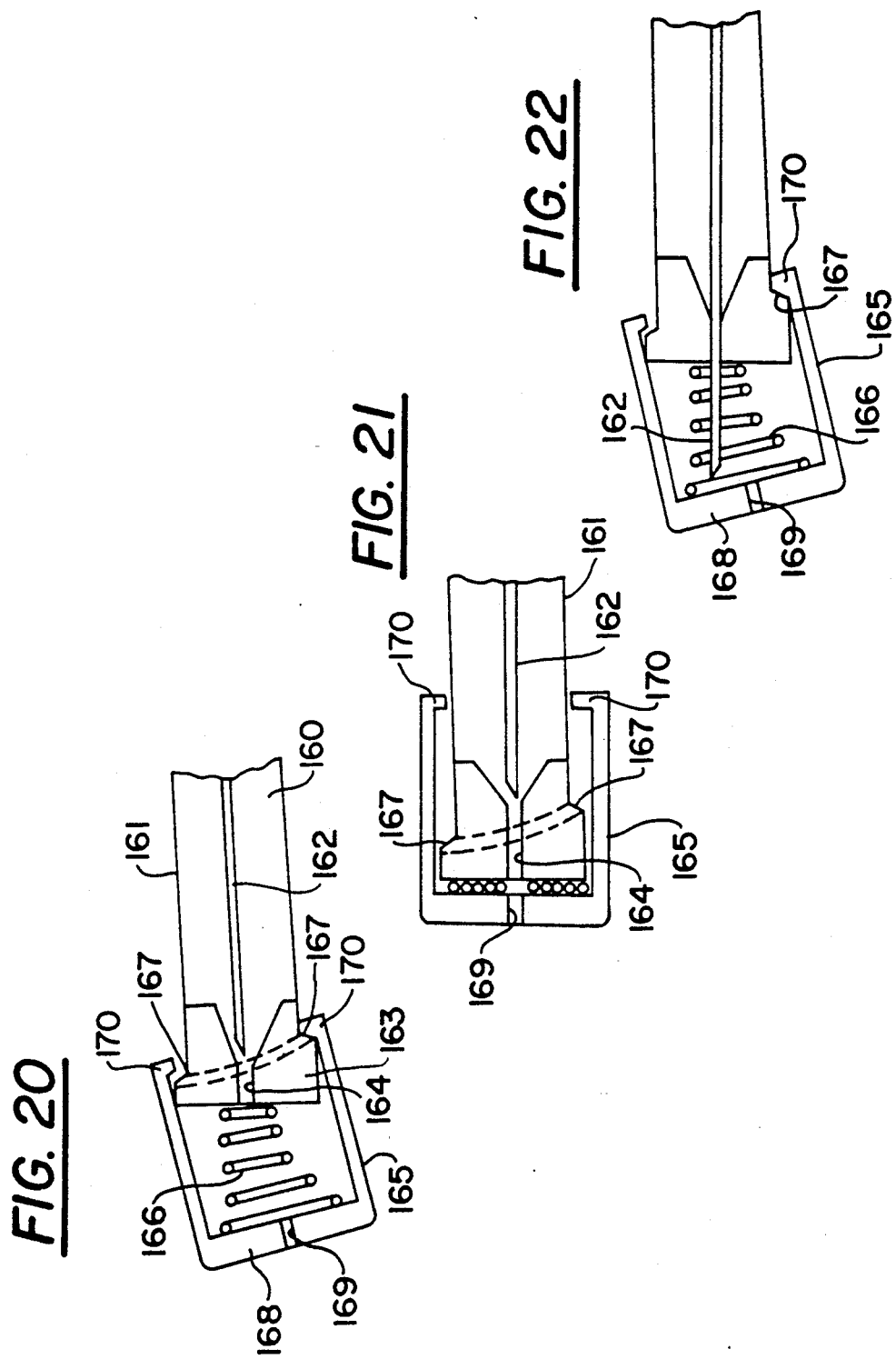

AUTOMATIC INJECTORS

This invention relates to automatic injectors of the kind comprising a body which contains a charge of medicament, a needle held in a sheathed position within the body, releasable drive means which when released drives the needle from its sheathed position to an unsheathed, projecting, position projecting from the body, and expulsion means for discharging the medicament through the needle. Automatic injectors of this kind will hereinafter be referred to as of the kind set forth.

Automatic injectors of the kind set forth have been developed primarily for use by persons who have to administer an injection into their own body at an instance which is not known beforehand. However, they may also be used by people who know that they will have to inject themselves, but are not skilled in the use of manually operated hypodermic syringes.

There are very many proposals for automatic injectors.

The aim of the present invention is to provide a new automatic injector which may be safer for use.

According to the invention we provide an automatic injector of the kind set forth characterised in that it has an associated protective, or sharps, assembly comprising a cover member and means to provide relative movement between the cover member and the needle of the injector, the arrangement being such that after the needle has been moved to its projecting position the sharps assembly is operable to provide relative movement between the projecting needle and the cover member such that the cover member covers the needle.

Preferably the needle reduces the chance of the user accidentally pricking themselves or others. However, the cover member may simply prevent the user from seeing the needle.

Despite the existence of many different kinds of automatic injectors hitherto they may have been a menace after use. Furthermore, after use the user can see the needle projecting from the body of the injector.

Preferably the cover member reaches the needle, and most preferably the cover member defines a cover space. The cover member is preferably movable relative to the body. Alternatively or additionally the needle may move relative to the body to effect relative movement between the needle and the cover member.

The cover member is preferably resiliently biased from a retracted, inoperative, position in which the needle can extend beyond it towards an extended, operative, position in which the needle does not extend beyond it.

The cover member is preferably rigid and may have a hole through which the needle extends during the injection process.

In the preferred embodiments of the invention the sharps assembly operates automatically after injection.

Thus the user does not have to take positive action to ensure that he is protected from the needle.

The cover member may have a pre-injection position relative to the body and be movable rearwards relative to the body to an injection position and may have a post-injection position in which it extends to or beyond the projecting position of the needle. The pre-injection and post-injection positions of the cover member may be substantially the same, at least longitudinally. Alternatively the pre-injection position of the cover member relative to the body may be further rearwards longitudinally of the injector than the position of the cover member in its post-injection position. This enables the unactuated injector to be more compact longitudinally than it would be if the pre- and post-injection positions were the same longitudinally. The pre-injection position of the cover member may be its injection position, or substantially its injection position. Alternatively the pre-injection position of the cover member may be between, longitudinally relative to the injector, the post-injection and injection positions. The pre-injection position may be about half, two-third, or four fifths of the way from the injection position of the cover member towards the post-injection position of the lower member.

The cover member may be moved to its injection position by the action of pressing the injector against the person of the user prior to activating the injector.

Preferably the cover member comprises a sheath, cap or tube, preferably retained to the body and axially movable relative thereto. The sheath is preferably movable between two axially spaced stops.

The cover member may have or be engaged by a manually releasable detent the release of which enables the sharps assembly to operate. The detent may comprise a tear-off tab, band or the like.

Preferably the cover member is lockable in its post-injection position. Alternatively the cover member may have a locked position which is different from the, unlocked, post-injection position, the needle still being protected in the locked position.

The cover member may be automatically locked after injection, or it may be manually lockable. The cover member may be locked by moving it axially or angularly, or a combination of both, relative to the injector body. For example, it could be locked following injection by moving it from its initial post-injection position further away from the body of the injector, or by turning it relative to the body. The locking mechanism could conveniently be one-way snap-engagement features, or a non-returnable ramp or cam system.

In the case of automatic operation of the sharps assembly and automatic locking of the cover in its post-injection position the user has substantially no opportunity of accidentally pricking anyone since the needle is effectively only out of the injector whilst it is in the user's body. This has a further advantage in that the needle can never be seen.

The injector may have locking means for the cover member comprising a snap-fit lock. The locking means may comprise a bayonet formation on the cover member or body.

Locking of the cover member may be effected by relative angular and/or axial movement between the cover member and the body.

Mis-alignment means may be provided between the cover member and the body to mis-align a needle aperture or weak area provided in the cover member with the (projected) needle after the injector has been fired, thereby preventing accidental relative movement of the cover member towards the body which could otherwise enable the projected needle to protrude beyond the cover member.

The mis-alignment means may comprise cocking, twisting, or tilting means adapted to tilt the cover member relative to the body to a non-coaxial configuration.

The mis-alignment means may mis-align the needle aperture, or weak area, in the cover member relative to the needle in the body when the injector is in its pre-firing, unoperated, state.

Embodiments of the invention will now be described by way of example only with reference to the accompanying drawings of which:

FIGS. 1 to 3 show schematically a first automatic injector in configurations, respectively, before use, during use, and after use;

FIG. 17 shows a modification of the injector of FIGS. 14 to 16;

FIG. 18 shows a section on the curved line from point A to point B of the modification of FIG. 17;

FIG. 19 shows a section on the curved line from point C to point D of the modification of FIG. 18; and FIGS. 20 to 22 show schematically a further modification of an injector in configurations, respectively before use, during use, and after use;

FIG. 23 shows yet another modification of an injector;

An automatic injector 1 is shown in FIGS. 1 to 4 which comprises an injector assembly 2, a plastics protective, sharps, cover member 3, and a sharps spring 4.

The injector assembly 2 is of a known general kind, and the particular details of its structure are not of prime importance to the broadest aspects of the invention. In the example of FIGS. 1 to 4 the structure of the injector assembly is generally the same as that described in our British Patent Application No. 9100819.3, but it will be appreciated that many other injector assembly arrangements can be used instead.

Figure 4:
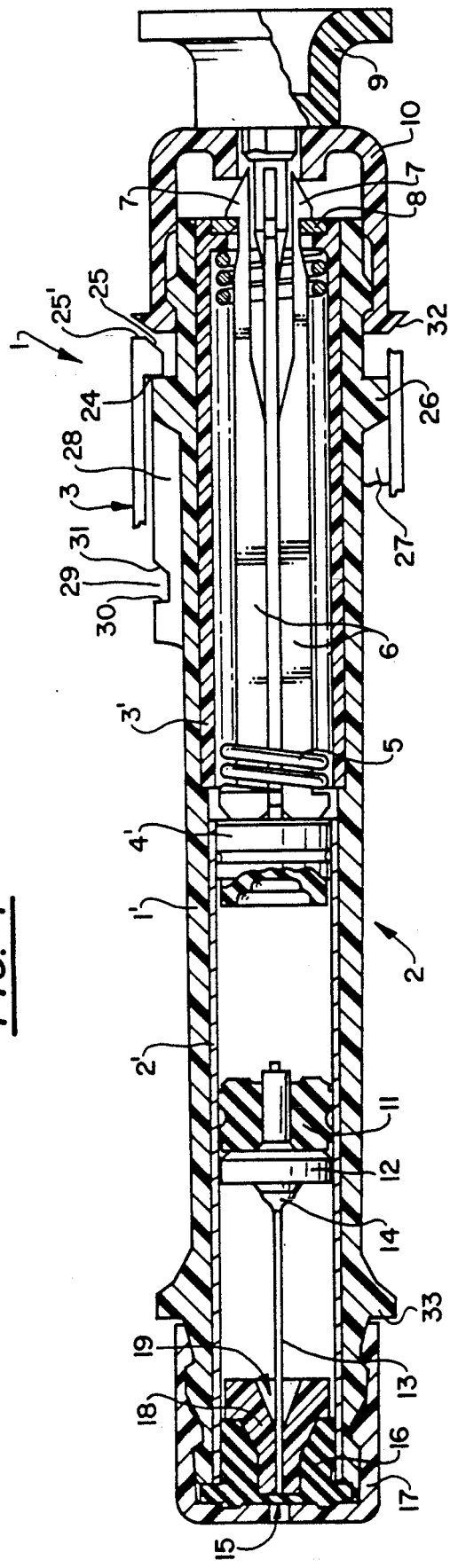
FIG. 4 shows detail of the automatic injector of FIGS. 1 to 3.

FIG. 4 shows details of the injector assembly 2 which comprises a body 1' of injection-moulded polystyrene containing a barrel liner 2' of F.E.P. 160 and a spring casing 3' of polystyrene. Sliding within the barrel liner 2' is a first piston 4' of rubber acted on by a stainless-steel coil compression spring 5. In the initial condition of the injector the spring is held in the compressed position, as shown in the drawing, by a collet 6 made in two halves having at their tail ends detent teeth 7 engaging a latch ring 8 seated in the end of the spring casing 3'. A safety pin 9 of moulded nylon normally keeps the teeth 7 apart but when it is withdrawn they can be urged together to release the collet 6 by a short movement of an end cap 10.

This spring-restraining and release mechanism is known and is substantially the same as that disclosed in our above-mentioned patent specification.

Also within the barrel liner 2' and spaced about half way along in the initial condition is a second piston 11, also of rubber. Sealed into this piston is a moulded polyethylene needle-mounting 12 carrying the injection needle 13 sealed into it by adhesive 14.

In the condition shown, the tip of the needle 13 stops just short of a diaphragm seal 15 formed in a bush 16 which is held in the end of the barrel liner 2' by an end cap 17.

The tip of the needle 13 is received in a guide 18 of HD polyethylene shaped as shown, with its outside fitting into the bush 16 and its inside a good sliding fit on the needle. At its inner end the guide has a convergent conical portion 19 which helps to lead the needle into the bore of the guide during assembly of the injector.

The space between the pistons contains the medicament and is in communication with the open rear end of the needle. The space between the second piston and the end of the body, i.e. the space around the needle, contains air or an inert gas.

When the injector is put to use by removing the safety pin 9 and actuating the end cap 10 to release the collet 6, the spring 5 initially advances both pistons together, as the liquid between them is virtually incompressible. The needle 13 advances through the guide 18 and penetrates the seal 15, emerging through the centre of the hole in the end cap 17. The air or gas in the space around the needle is able to force its way between the outside of the needle and the bore of the guide 18, and so does not hold up the advance of the second piston. This is an important feature of the injector assembly 2 (but not necessarily of the present invention) and it means that the needle is able to advance fully into the patient's body until brought to halt when the mounting 12 comes up against the guide 18, and thereafter medicament is injected by the continued advance of the first piston. Only a negligible quantity, if indeed any at all, is injected during the advance of the needle.

The cover member 3 substantially surrounds the body 1' and has side walls 20 of larger internal diameter than the outer diameter of the body 1, a front end face 21 having a central hole 22, and carries one or more resilient deflectable fingers 23 at its rear end. The finger 23 has a latching face 24 and a chamfered face 25.

The body 1' of the injector assembly 1 has at its rearward end a radially projecting latching rib 26 and one or more guide fins 27,28 extending radially outwards adjacent the rib 26. At least one of the fins, fin 28, has a recess 29 axially spaced from the rib 26 and defines forward and rear abutment faces 30 and 31. The rearward end cap 10 has a chamfered end face 32. The forward end of the body is provided with an abutment rib 33 adjacent the end cap 17. The spring 4 surrounds the end cap 17 and abuts against the rib 33, continually urging the end face 21 of the cover member 3 away from the body 1.

In the pre-injection condition shown in FIG. 1 the finger 23 is latched onto the rib 26 and the cover member 3 is held in place against the end cap 17, with the spring 4 compressed.

When the user wishes to use the injector he places the end face 21 against his leg (or other body part, or against the body of someone else to be injected), then removes the safety pin 9 and presses the end cap 10. The face 32 engages the face 25 and biases the finger 23 radially outwards, releasing the finger from its engagement with the rib 26. Simultaneously the spring 5 is released and the needle 13 is driven through the hole 22 and into the user. The hole 22 may be covered by a membrane for hygiene purposes.

Since the end face 32 of the cap 10 is now adjacent the rib 26, as shown in FIG. 2, when the user moves the injector away from his leg the head of the finger 23 cannot return to its radially inward position of FIG. 1 (there is not a big enough gap between the rib 26 and the end cap 10) and the spring 4 moves the cover member forward to its advanced position shown in FIG. 3 in which the needle 13 is held in a chamber 34 defined by the cover member. The head of the finger 23 is received in recess 29 and the face 24 of the finger 23 is engaged against face 30 and this restrains further forward movement of the cover member.

In the embodiment of FIGS. 1 to 4 the cover member 3 is advanced automatically, but it may possibly be moved manually back against the action of spring 4 because of the possibility of co-operation between the sloping faces 24 and 31.

In a modification the face 31 is not sloped, instead it forms an abutment preventing the return of the finger in an axial direction. For example the flat end face of the finger, referenced as 25' in FIG. 4, may abut a complementary radial face. Thus the sharps system is locked in its needle-covering position.

Figure 5:
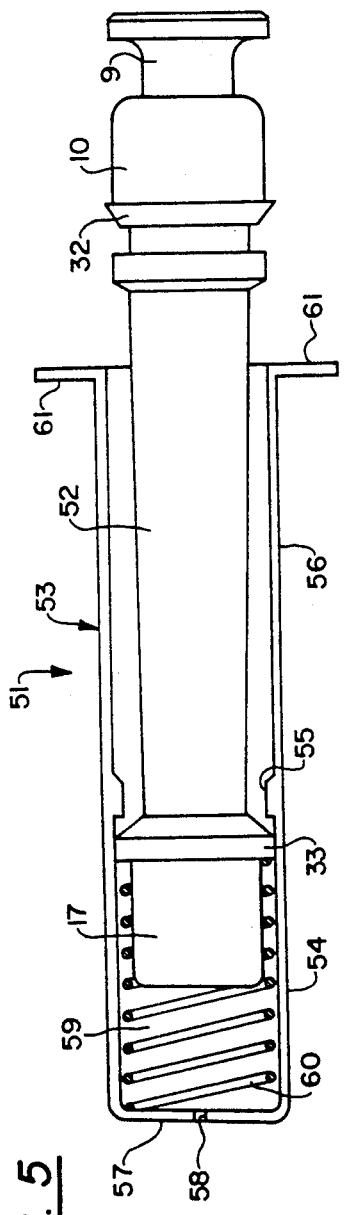
FIGS. 5 to 7 show schematically a second automatic injector in configurations, respectively, before use, during use, and after use.
Figure 6:
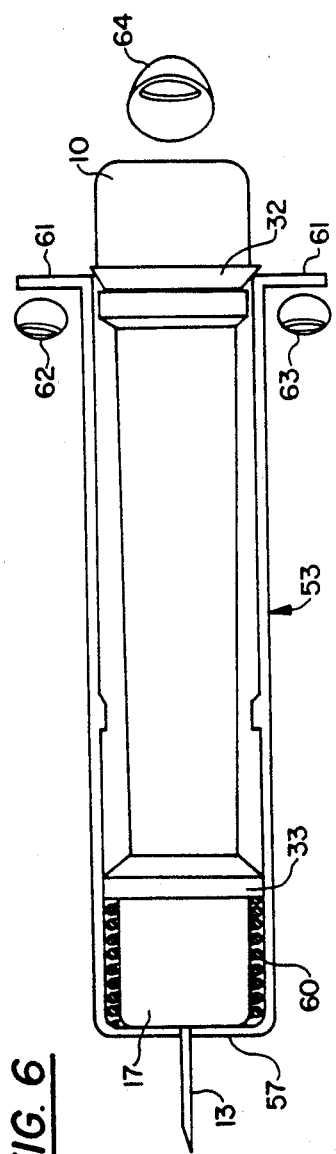
Figure 7:
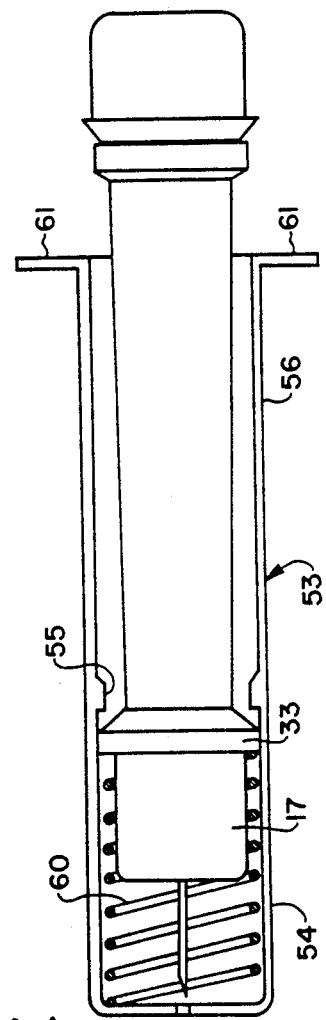

FIGS. 5 to 7 show another automatic injector 51 incorporating an automatic sharps system. The injector 51 comprises an injector assembly 52 which is similar to the assembly 2 of FIG. 4, (and similar components have been given the same reference numerals) and a generally cylindrical cover member 53. The cover member 53 has a forward portion 54, an internal annular abutment ridge 55, and a rearward portion 56.

The forward portion 54 has a front end wall 57 provided with a central hole 58 and in the pre-injection condition shown in FIG. 5 defines a space 59 between the forward end cap 17 of the assembly 52 and the front end wall 57. A spring 60 engages the wall 57 and the abutment rib 33 of the injector assembly 52 and continually urges the wall 57 away from the rib 33.

The rearward portion 56 of the cover member 53 has a pair of radial arms 61 extending away from it at its rearmost end, which is open. The injector assembly 52 is received in the cover member 53 and is substantially surrounded by it, the end cap 17 of the injector assembly 52 being held in the space 59 by the ridge 55.

To use the injector 51 the user places the front wall 57 of the member 53 against his, or someone else's, body part, removes the safety pin 9, places his index finger 62 and middle finger 63 in front of the arms 61, and his thumb 64 on the rear end cap 10, and then presses the end cap 10 with his thumb, in the manner of operating a manual hypodermic syringe.

The initial phase of pressing of the cap 10 compresses the spring 60 until the front end cap 17 engages the wall 57. The second phase of pressing the end cap 10 releases the detent teeth 7 and spring 5 of the injector assembly 52, thereby firing the needle 13 into the user's body and injecting the contents of the injector. The strength of the spring 60 and the force necessary to release the detents 7 are arranged appropriately for the spring 60 to be compressed before the spring 5 is released.

When the user removes the injector for disposal the spring 60 moves the cover member 53 over the needle and surrounds the needle with the rigid forward portion 54.

Figure 8:
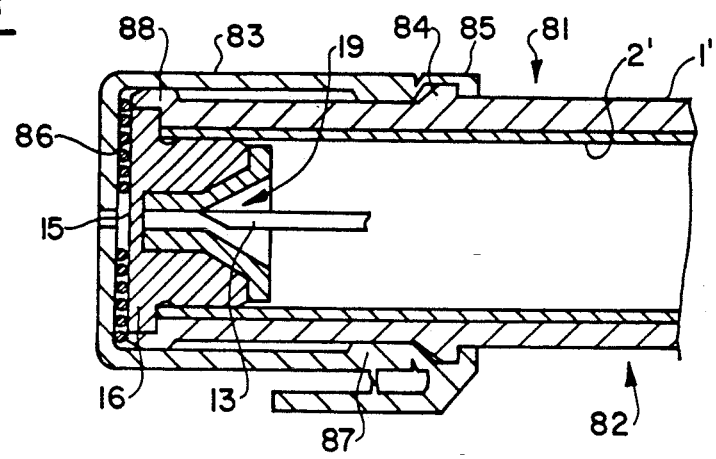
FIGS. 8 to 10 show schematically details of a safety assembly of a third automatic injector in configurations, respectively, before use, during use, and after use.
Figure 9:
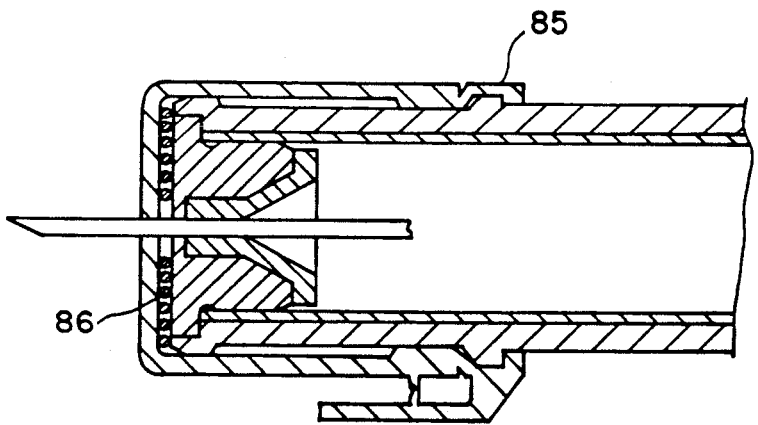
Figure 10:
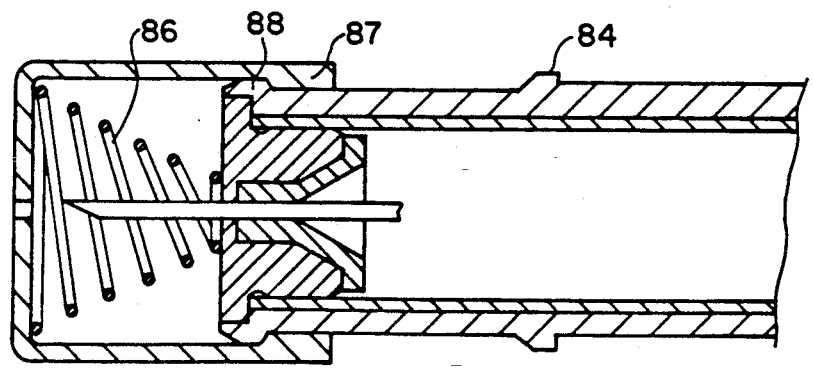

FIGS. 8 to 10 show a modified injector 81 having an injector assembly 82 and a cover member 83 attached to the end of a body 1' of the assembly 82. The assembly 82 is very similar to that of FIGS. 1 to 4 and the same reference numerals have been given to similar components.

The body 1' of the assembly 82 has an external flange 84 which co-operates with a tear-off strip 85 of the cover member 83. The cover member 83 can be considered to be similar to end cap 17 of the arrangement of FIG. 4, except that it is biased by a spring 86 away from the bush 16. The spring 86 engages the end of the body 1' and the inside of the end wall of the cover member 83.

The injector 81 is used in the same way as the injector of GB 9100819.3, except that after injection the user tears off strip 85 which releases the spring 86 and causes the cover member 83 to move forward and enclose the projected needle. The cover member 83 and body 1' have complementary lugs 87 and 88 which prevent relative longitudinal movement beyond the position shown in FIG. 10.

Figure 11:
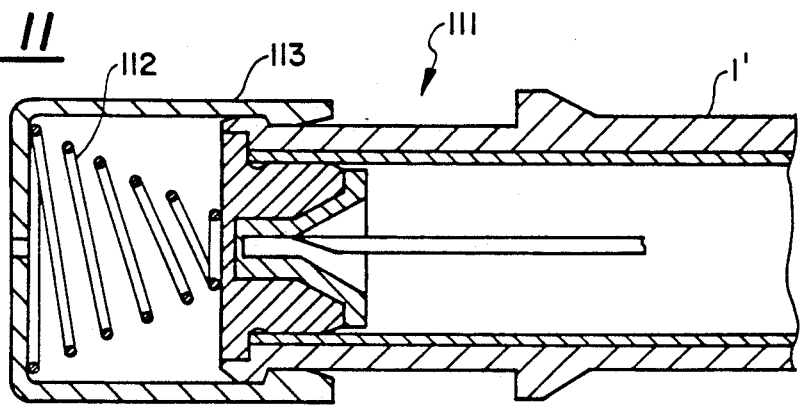
FIGS. 11 to 13 show schematically details of a safety assembly of a forth automatic injector in configurations, respectively, before use, during use, and after use.
Figure 12:
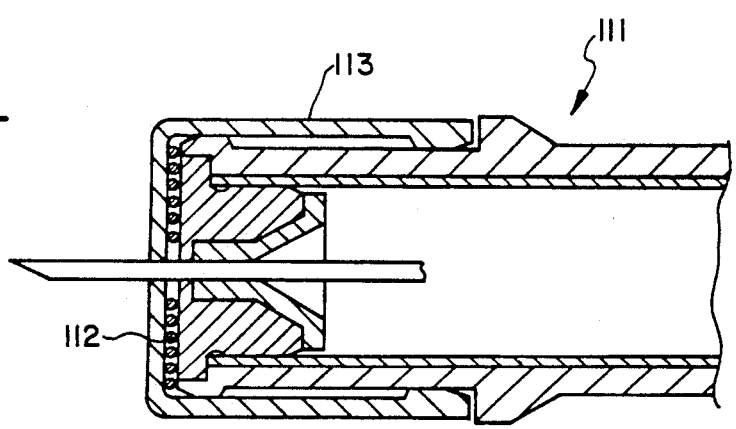
Figure 13:
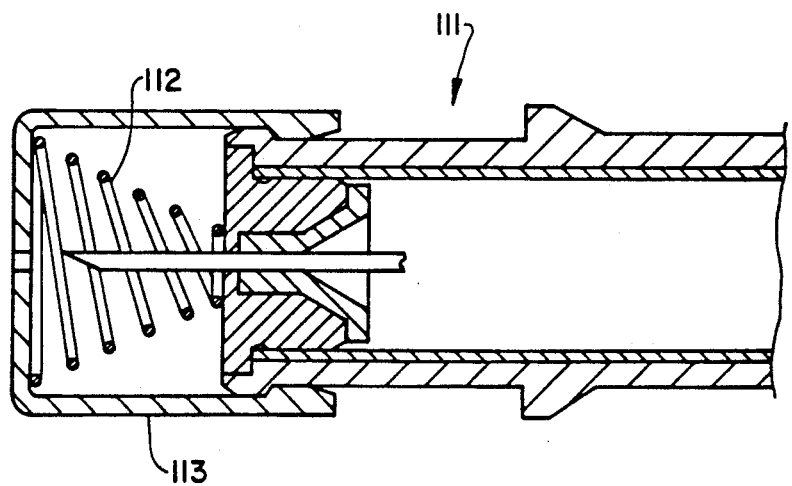

Alternatively the strip 85 could be torn off before use, which would give an injector similar to the injector 111 illustrated in FIGS. 11 to 13. The injector 111 has a spring 112 and a cover member 113.

Injector 111 can be arranged to operate in a similar manner to injector 51 in that its spring 112 is compressed by the action of pressing on its rear end cap, actuation of the injector occurring after the injector assembly has moved towards the cover member. Alternatively, the user may push the cover member 113 of the injector 111 against his person by holding the sides of the body 1' and then actuate the injector. This could, of course, also apply to the injector 51.

Figure 14:
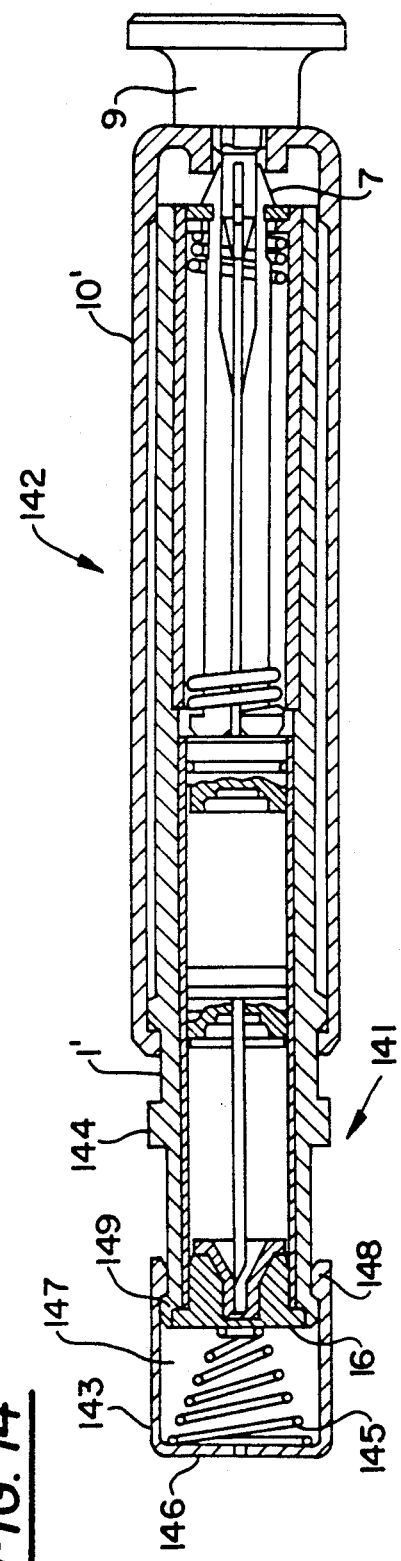
FIGS. 14 to 16 show schematically a fifth automatic injector in configurations, respectively before use, during use, and after use.
Figure 15:
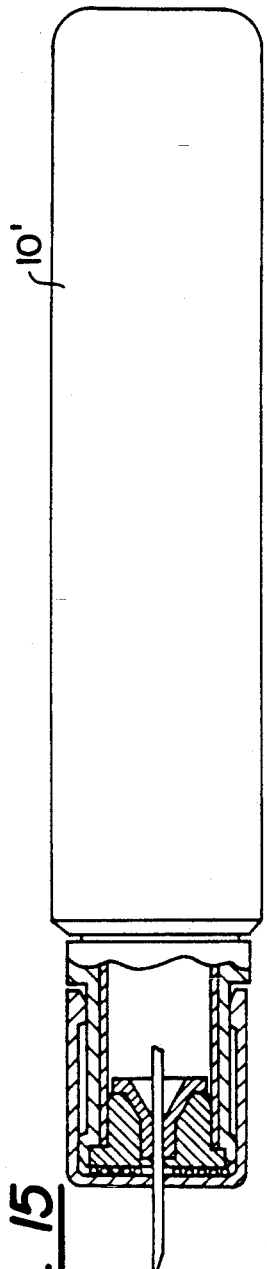
Figure 16:
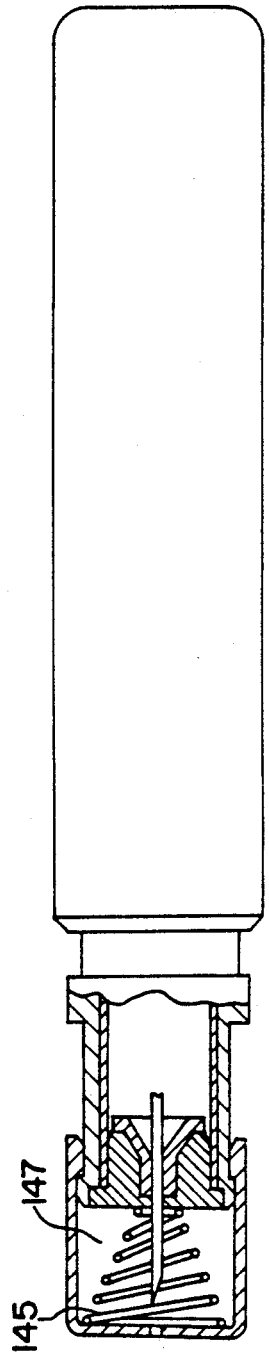

FIGS. 14 to 16 show an injector 141 having an injector assembly 142 and a cover cap or member 143. The injector assembly is largely as shown in our published European Patent Application No. 0 361 668, the contents of which are hereby incorporated by reference.

The assembly 142 comprises many components similar to those of assembly 2 and similar components have been given the same reference numerals.

The body 1' of the injector assembly 142 has towards its forward end an abutment flange 144. The rear end cap, referenced as 10', is longitudinally elongated and extends from the rear end of the body 1' to just before the flange 144 (in the pre-injection position shown in FIG. 14). A spring 145 bears against an end wall 146 of the cover member 143, and against the bush 16, and continually biases the cover member 143 away from the body 1' so as to define an enclosure 147. The cover member 143 has an annular projection 148 at its rear end which co-operates with a complementary projection 149 on the end of the body 1' to retain the member 143 to the body.

The user places the wall 146 against the area to be injected, removes the safety pin 9 and presses on the rearmost end of the end cap 10'. The spring 145 is compressed until the end of the cylindrical side walls of the cover member 143 engage the flange 144 whereafter force is transferred back to the detents 7. Further pushing on the end cap 10' causes the detents 7 to be released, the needle to be injected into the recipient, and the contents of the injector 141 to be injected. After removal of the injector from the user's body the spring 145 moves the cover member 143 over the needle to hide it.

Any or all of the injectors described could have a locking arrangement for their cover members such that once the cover member moves so as to hide the needle after injection it can be manually, or automatically, locked against retraction such as would expose the needle again.

A locking condition of the cover member may be achieved in substantially the post-injection positions shown in the drawings, or there may be further relative movement between the cover member and the body to a locked position.

One possible automatic locking mechanism is shown in FIGS. 17 to 19. For the sake of convenience the arrangement will be described with reference to the embodiment of FIGS. 14 to 16, but the structure is of course applicable to any of the injectors.

The cover member 143 has means, bayonet means 150, which co-operates with means, track or groove means 151, provided at the end region of the body 1' such as to provide a one-way path to a locking position as the cover member 143 is moved towards the body 1' and then released away from it again.

The bayonet means 150 comprises a stud 152 projecting radially inwards from the ring of the annular projection 148. The cover member 143 has a longitudinal slot provided in it adjacent the stud 152 so as to enable the side wall of the member 143 which carries the stud 152 to flex radially outwards, as will be described.

The track means 151 comprises a portion 153 extending rearwards, and a portion 154 extending back forwards. A locking hole 155 is provided at the forward end of the portion 154. The locking hole 155 has a step 156. The rearwardly extending portion 154 of the track 151 has a sloping base which is deeper at its forward end, and reaches its shallowest point (referenced as 157) before its rearmost point, and then becomes deeper again. This is the portion A to B shown in FIGS. 17 and 18.

The forwardly extending portion 154 of the track 151 has a base which slopes from a shallow end (point B) spaced from the forward end of the body 1' to a deeper end (point D) adjacent the forward end of the body. The locking hole 155 is at the deeper end of the forwardly extending portion 154. The rearwardly extending portion 153 is curved and bends to meet the forwardly extending portion 154. Of course, the track 151 could have regions where its base is flat.

In use, as the cover member 143 is moved towards the body 1' the stud 152 rides up the slope of the rearwardly extending portion 153 of the track until it reaches point 157, the side wall of the cover member flexing radially outwards, and then rides down the slope beyond point 157 and around the bend in the rearwardly extending path 153. As the cover member moves forwards relative to the body 1' the stud 152 has a tendency to move "downhill", which guides it to move along the portion 154 of the path, rather than returning along portion 153. The stud 152 snaps into hole 155 and the step 156 prevents the cover member from being pushed back again relative to the body 1'.

It will be appreciated that in the embodiments of FIGS. 1 to 4, and 8 to 10, where the cover member does not move towards the body before being advanced, there is no need for such a complicated one-way track. The locking means could simply comprise the forward portion of the track.

Of course, the stud could be on the body and the track in the cover member. There may be more than one stud and associated track. The forwardly extending portion of the track may be curved, either in addition to or instead of the rearwardly extending portion (when provided)

FIGS. 20 to 22 show another modification which is applicable to any of the injectors described. FIG. 20 shows an automatic injector 160 before use. The injector 160 has a body 161, a needle 162, a needle guide 163 having a needle hole (or thin-walled region) 164, a cover member 165, and a spring 166. The front end of the body 161 has a flange or shoulder 167 which is inclined relative to a plane normal to the needle 162. The cover member 165 has a front wall 168 having a through-hole (or a thin walled region) 169 through which the needle 162 extends in use, and a rearward flange 170 which co-operates with a flange 167 of the body. There may be a membrane (which may be similar to seal 15 of the arrangement of FIG. 4) provided at the forward end of the injector, the needle piercing the membrane during injection.

The spring 166 urges the front wall 168 away from the body 161, with the flange 170 engaging against the rearmost portion of the flange 167. Since the flange 167 is angled relative to the body (it is not perpendicular to it) the cover member 165 is urged by the spring 166 to a cocked position, shown in FIG. 20, until the flanges 170 and 167 engage at both sides of the body (at the top and bottom as seen in FIGS. 20 to 22). The hole 169 is mis-aligned with the hole 164.

When the user presses the wall 168 against his leg the cover member 165 is moved towards the body 161 and the cover member and body take up a concentric configuration, with the holes 164 and 169 aligned as shown in FIG. 21.

When the automatic injector operates the needle passes through the holes 164 and 169 into the user's body (and through any sealing membrane which may be provided).

When the user removes the used injector from his body part that has just been injected the spring 166 pushes the cover member 165 to its advanced position. As the cover member slides forwards the needle 162, which is projecting from the body, keeps it concentric with the body until the wall 168 moves beyond the forwardmost tip of the needle whereafter the spring 166 again causes the cover member to take up its cocked configuration because of the inclined flange 167. Accidentally pushing on the front wall 168 of the cover member now causes the wall 168 to engage the needle and this stops the cover member from being moved further towards the body and ensures that the needle is safely covered. Accidental re-location of the needle 162 in the hole 169 is very unlikely and the mis-alignment of the needle and hole 169 effectively serves as a lock for the cover member.

Of course, the flange 170 could be inclined so as to serve as mis-alignment means, either in addition to, or instead of, the inclining of flange 167.

The forward end portion of a modified injector 180 is shown in FIG. 23. The injector 180 has two modifications of note, the first of which is that instead of having an end cap with a small needle aperture to define a sharps enclosure for the needle, it has an open-ended sheath, sleeve, or tube, 181. This may be easier or cheaper to manufacture. The protective sheath 181 may need to project further than an equivalent end cap with a substantially closed end in order to protect the needle properly. It may even be acceptable to allow a user deliberately to insert his finger into the open end of the sheath and reach the needle, so long as it is unlikely to occur accidentally. On the other hand the sheath 181 may be too narrow or too long (in its advanced position) to allow an adult, and/or a child, to push their finger inside it and reach the needle after firing of the injector.

The injector 180 also has a second difference from those previously described and that is that the rear end of the sharps spring 182 (which urges the sheath forwards) bears against a plastics or metal load-spreader plate 183 which in turn bears on the rubber bush 16. This spreads the load of the spring and avoids the bush 16 deforming locally as it might if the spring 182 were to contact it directly (and over a smaller area). The load spreader plate 183 may engage a radial shoulder on the forward end of the body 1', thereby transferring force directly to the body, without stressing the bush 16 significantly. Alternatively, another way of avoiding applying excessive load to the rubber bush 16 is to have the plate 183 integral with the body 1' of the injector. This is effectively mounting the spring 182 on an end cap of the injector.

In the arrangement of FIG. 23 the spring 182 bears against a circlip 184 received in a groove in the inner wall of the sheath 181. The circlip 184 and/or spring 182 may serve as an obstacle to the user's finger if the user tries to reach the needle.

It will of course be appreciated that the feature of an open-ended sheath providing the cover member for the needle, and the feature of the spring bearing on a load-spreader plate, or an end cap of the injector, can apply to any of the embodiments described.

Figure 24:
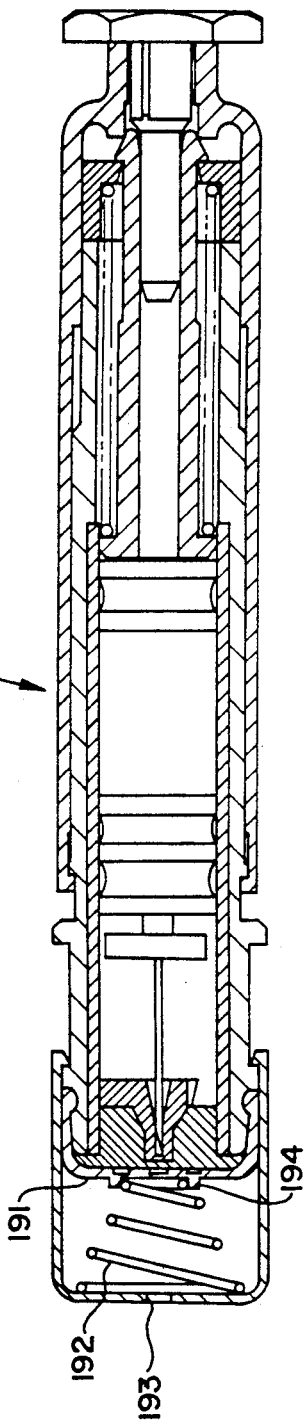
FIG. 24 shows a modification of the injector of FIGS. 8 to 10.

FIG. 24 shows an arrangement similar to the arrangement of FIGS. 8 to 10, but modified along the lines mention above. The injector, referenced 190, has a rigid plastics material end cap 191 similar to that disclosed in our co-pending patents already referred to, and a spring 192 urging a sharps cover 193 away from the end cap 191. The end cap has a centering, or retaining, ring 194 moulded on its forward face which serves to locate one end of the spring 192. The end cap 191 is permanently fixed to the body of the injector.

Figure 25:
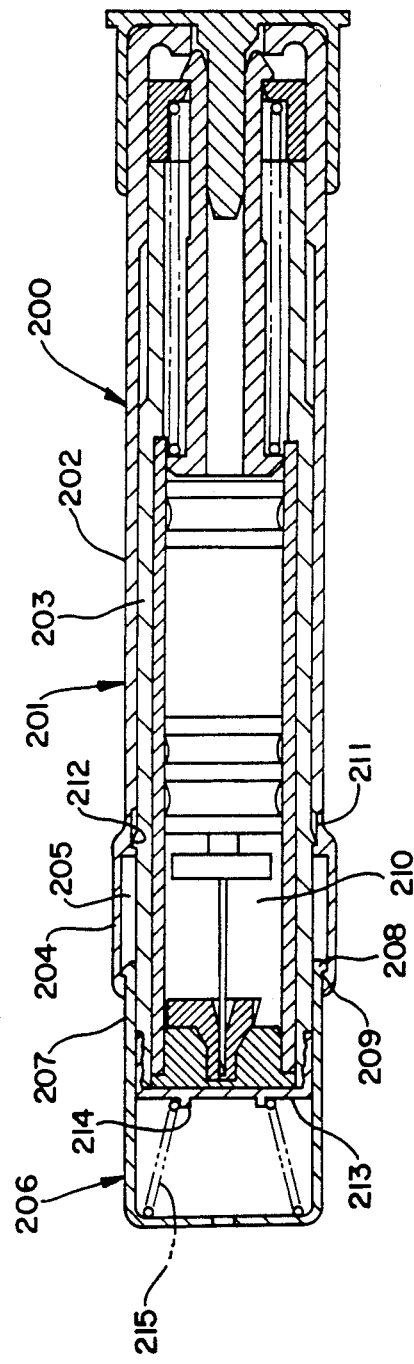
FIG. 25 shows detail of another injector.
Figure 26:
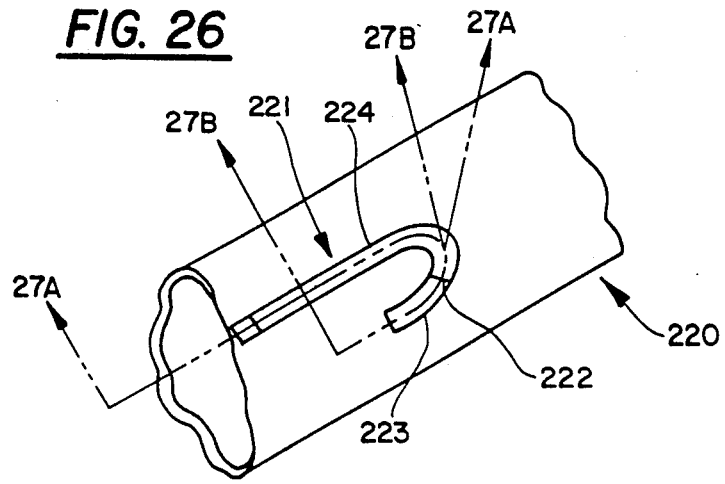
FIG. 26 shows a modification of the injector of FIGS. 17 to 19.
Figure 27A:
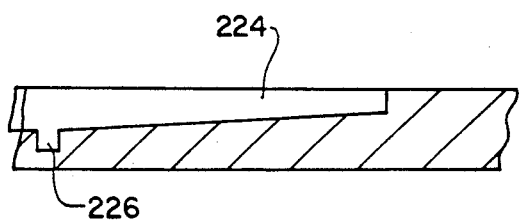
FIGS. 27A and 27B show cross-sections on curved lines 27A—27A and 27B—27B of FIG. 26.
Figure 27B:
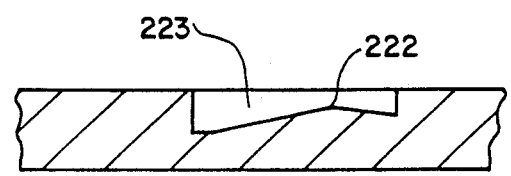
Figure 28A:
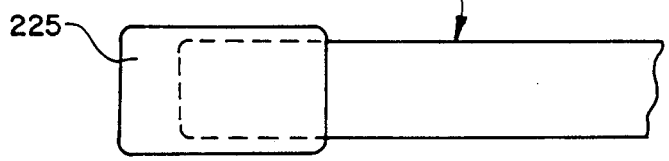
FIGS. 28A to 28C show schematically the forward end of the injector of FIG. 26 in its pre-injection, during-injection, and post-injection positions respectively.
Figure 28B:
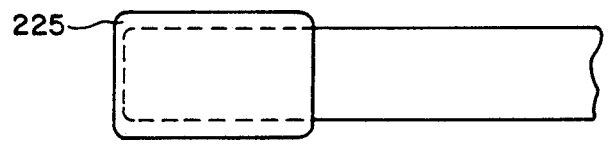
Figure 28C:
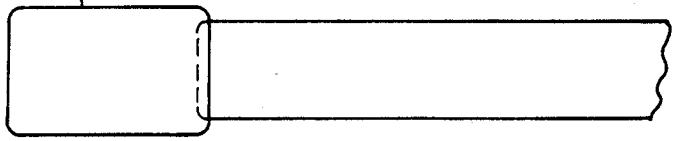

FIG. 25 shows another injector 200. The injector has a body 201 formed from an outer tubular member 202 and an inner tubular member 203. The outer member 202 is provided with a collar 204 which defines in part an annular space 205. The inner member 203 also helps to define the space 205. A sharps cover 206 is provided extending over the forward end of the inner member 203. The cover 206 has sidewalls 207 which are capable of entering the space 205, and retaining formations 208 which are trapped in the space 205 by a shoulder 209 provided on the collar 204. The collar 204 is in this example provided on the outer tubular member 202 and the separate inner member 203 which contains a medicament chamber 210. The outer member 202 has an annular groove 211 which receives projecting locating formations 212 of the inner member 203 in a snap-fit manner. The outer member 202 can move slightly axially relative to the inner member 203 to actuate the injector. The injector has an end cap 213 which has a locating formation 214 to locate a spring 215 which bears against the cover 206.

In use the rearward part of the side walls of the cover slide into the internal space 205. Because the cover 206 slides in an internal space the space cannot easily become blocked with dirt or other obstructions.

The arrangement of FIG. 25 is front actuated in that the user must press the front of the injector against his body for the injector to operate. The cover 206 must therefore be in its retracted position for the injector to operate. It is not possible for the user to actuate the injector without retracting the cover 206. This avoids any possibility of the user injecting into the space defined by the cover member when it is in its advanced position. Similarly it is very difficult for a user to actuate the injector of FIG. 24 without compressing the cover member. The only way he can do it is to grip the body of the injector just behind the cover member 193. This is unlikely to occur accidentally. Furthermore, the injector of FIG. 24, and indeed any of the automatic injectors, can be made front actuated fool-proof injectors by using the principle of an outer sleeve extending substantially the full length of the injector as exemplified in FIG. 25.

FIGS. 26 to 28C illustrate a way of reducing the axial length of an injector having a sharps system. It is desirable to have an injector in accordance with the invention, but which is not too much longer than a comparable injector which does not have the sharps system. The injector, referenced as 220, has a guide track 221 comparable with track means 151 of the embodiment of FIGS. 14 to 16. However, instead of the track 221 having rearwardly and forwardly extending portions, 223 and 224 respectively, of equal longitudinal, axial, length, the forward portion 223 takes the cover member (referenced as 225 in FIGS. 28A to 26C) further forwards than it is in its pre-injection position. The track has a double cam, with crest 222 being shown. The cover member can be considered to be about 80% retracted towards its injection position (20% advanced towards its post-injection position) in its pre-injection position.

There is a snap-fit lock 226 (see FIG. 27A) operable at the post-injection position to prevent the cover member from being retracted again. The cover member 225 has a pin, or the like, which is guided in the track 221, and locking means (usually the guide pin) which cooperates with the snap-fit lock 226.

There may also be a lock, or releasable latch means, to hold the cover in its pre-injection condition against accidental movement therefrom. The pre-injection latch could comprise a component which is manually destroyed before the injector is used (such as a tear-off band), or it could comprise a snap-fit latch, for example a stud engaged in a complementary hole.

It will be appreciated that it is preferable to have the spring which engages the sharps cover member weaker than that the force necessary to be applied to the rearward end cap of the injector to actuate it. This means that when the injector is placed against a user and its rearward end cap is pressed to actuate the injector, the injector will fire only after the sharps cover member has been fully retracted.

The sharps cover member may be manufactured by moulding it as a cylinder. Alternatively we may find it better to mould it as two half-cylinders, possibly joined by a living hinge, and to join the two half cylinders together around the forward end of the body of the injector to assemble the sharps cover member, and simultaneously attach it to the body of the injector. The two half-cylindrical portions of the sharps cover member may have complementary interengagable snap-fit formations to enable the two halves to be joined together with a snap-fit operation.

We may also care to mould the sharps spring into the sharps cover member. There may be a plastics moulding spring.

Another arrangement for a fully automatic sharps system for an automatic injector comprises having a resilient compressible member, such as a foam sponge or the like, mounted at the front end of the injector (for example bonded to the front end cap, such as cap 17 of FIG. 4). When the injector is unactuated its front end (i.e. the resilient compressible member) can be pressed against the user's body prior to release of the drive means, compressing the axial length of the resilient compressible member, and thereby bringing the user's body part within range of the needle when the injector is actuated. Upon actuation the needle passes through the resilient compressible member, which may have a hole to assist this, and into the user's body part. As the user moves the injector away from his body after injection the resilient compressible member expands again to cover the needle. Thus after use the needle is encased in the resilient compressible member, giving sharps protection—or at least a degree of protection. The needle is hidden by the resilient compressible member and can never be seen.

Instead of having a resilient compressible member which is compressed in use and then expands, the injector could be provided with an expandable member which is in a compressed condition, or a partially compressed condition, during storage of the injector (and during an injection) and which is released to expand and cover the needle after injection. The expandable member preferably expands automatically after injection to provide an automatic sharps system. The expandable member may comprise a resilient material, such as a foam sponge.

The resilient compressible member or expandable member could be provided as the cover member, or inside or behind a more rigid cover member (thereby acting as a spring).

A further modification may be to have the resiliently compressible member, or expandable member, comprise a helical spring. The coils of the spring can take the place of side walls of a rigid cover member, the released spring surrounding the needle and thereby comprising a cover member. The spring may have an open end (akin to the arrangement of FIG. 23) or it may have an end plate with a needle aperture. Even though a tubular spring surrounding a projecting needle is not rigid it can still be an effective cover member, for example the end plate could have its needle aperture mis-aligned with the needle after injection. The spring could have a bent, non-straight, relaxed condition. The spring could be a conical spring so that the projected needle cannot be seen between the coils of the expanded spring, or at least is substantially obscured from view.

The sharps assembly, of whatever kind, may be released for movement by the action of injecting. For example it may be released (as in the arrangement of FIG. 26) by the rearward movement of the cover member. Alternatively the sharps assembly may have release means actuated by movement of the drive means or expulsion means.

In yet another embodiment of the invention an automatic injector may have a cover member screw-threaded onto the forward end of the body of the injector. Automatic unscrewing means (such as a spiral/-torque spring) is provided acting between the cover member and the body. The cover member has a release feature akin to that of FIGS. 17 and 26 in that the cover member is initially in an intermediate axial position, pressing the cover member against the user's body moving the cover member back a distance (say 20% of its eventual forward travel). This rearward movement of the cover member releases the screw-action locking mechanism—(it may allow the screw thread on the cover member to engage the rear portion of the screw thread on the body, or they may already be interengaged). After the injector has been fired it is removed from the skin. The automatic unscrewing means operates to unscrew the cover member thereby extending the cover member forwards. The screw threads have a sufficiently low helix angle that when the cover member is extended merely pressing it back axially has little effect: an angular torque is required for ease of movement. This is less likely to happen accidentally.

The automatic unscrewing means may advance the cover to such an extent that it is fully unscrewed from the thread on the body—the screw threads may no longer co-operate. The cover member is then, of course, still retained to the body by retaining means to stop it falling off. Since the screw threads of the cover member and body do not now mate the cover member cannot be accidentally pushed back to reveal the needle. Thus the screw threads provide automatic locking of the cover member in a needle-protecting position (even though the cover member may not be rigidly held to the body it is still prevented from exposing the needle accidentally).

Any of the features of any one of the injectors disclosed may be used in combination with another injector.

Tear-off bands are considered advantageous because they can be used to keep an injector in a retracted, compressed, condition prior to use, and so keep the part of the injector against which the cover member slides covered up so that it cannot become clogged up with dirt or other obstructions. A tear-off band could be used even when the injector has its cover member in an advanced, or partially advanced, position when the injector is in its storage condition simply to ensure that the area of the injector body that is to have the cover sliding back over it in use is not liable to become blocked. The tear-off band could be removed immediately prior to using the injector. Preferably removal of the band enable the injector to be actuated. A tear-off band, or some other lock, is very useful on automatic injectors which have sharps systems which lock in place when fully advanced in order to prevent accidental movement of the sharps cover to the advanced position before the injector is used (thereby locking the cover in its advanced position and making the unactuated injector unusable).

A particular advantage of an automatic injector which has an automatic sharps system is that the needle is never seen by the user. The only time that the needle protrudes from the injector is when it is in the user's body. As discussed, this improves the safety of the system. A further advantage is the very fact that the needle is not seen by the user. Some people are afraid of needles and it can be comforting not to have to see them. This can allow some people to use injectors who would otherwise be psychologically unable to use them.

One of the areas where we see our automatic injectors having an automatic sharps system being used is to combat male impotence. A man can simply place an automatic injector at the base of his penis and inject himself without needing any particular skill and he need never see the needle. This can readily be appreciated as being an advantage for this particular use, given the natural fear of placing exposed sharp objects near the genitals.

The invention can also be used with automatic injector systems which have a pre-filled syringe which is loaded into a re-usable or single use firing mechanism.

I claim:

1. An automatic injector comprising:
   a body;
   a charge of medicament contained in said body;
   a needle held in a normally sheathed position within said body and being driveable into an unsheathed projecting position from said body, said needle having a substantially constant diameter along a length thereof and terminating at a point at a forward end thereof;
   a rigid cover member capable of movement relative to said body from an inoperative position to a protective position in which said cover member is capable of covering said needle when said needle is in said projecting position from said body, said cover member being generally concentrically disposed about a longitudinal axis of said body and having an opening in a portion thereof adapted to engage a general area of flesh to be injected by said needle, said opening having substantially the same diameter as said needle;
   releasable drive means for driving said needle from said sheathed position to said unsheathed, projecting position from said body and through said opening in said cover member, said releasable drive means further forcing said medicament through said needle; and
   biasing means for moving said cover member relative to said body into said protective position in which it covers said needle when said needle is in said unsheathed projecting position.

2. The injector as claimed in claim 1 further comprising restraining means for restraining said cover member from being moved into said protective position prior to said needle being driven into said unsheathed projecting position.

3. The injector as claimed in claim 2 further comprising activating means for releasing both said releasable drive means and said restraining means.

4. The injector as claimed in claim 3 wherein said releasable drive means and said restraining means are released simultaneously.

5. An injector as claimed in claim 3 wherein said biasing means urges said cover member against said surface to be injected after said surface is engaged and said restraining means is released.

6. The injector as claimed in claim 1 wherein said releasable drive means comprises manually releasable detent teeth for actuating said automatic injector when released.

7. The injector as claimed in claim 6 further comprising teeth for securing said detent means in an unreleasable condition and rendering said automatic injector inoperable.

8. The injector as claimed in claim 1 wherein said biasing means is in a fully compressed state prior to an injection operation.

9. An injector as claimed in claim 1 wherein said releasable drive means comprises a spring.

10. An injector as claimed in claim 2 wherein said restraining means comprises a latching surface disposed on said cover, said latching surface being cooperable with a latching rib disposed on said body to maintain said cover in said inoperative position prior to said needle being driven into said unsheathed projecting position.

11. An injector as claimed in claim 1 further comprising locking means for locking said cover member in said protective position so as to restrain said cover member against movement which would expose said needle after said injection operation.

12. An automatic injector comprising:
    a body having a longitudinal axis;
    a charge of medicament contained in said body;
    a needle held in a normally sheathed position within said body, said needle having a substantially constant diameter along a length thereof and terminating at a point at a forward end thereof;
    a releasable spring for driving said needle from said sheathed position to an unsheathed, projecting position in which said needle projects from said body, said releasable spring being operable to force said medicament through said needle;
    a protective assembly comprising a cover member having a sleeve-like first portion generally concentrically disposed about said longitudinal axis of said body and a second portion adapted to engage a general area of flesh to be injected by said needle, said second portion having an opening therein with substantially the same diameter as said needle, said cover member being capable of axial movement relative to said body and having a protective position in which it covers said needle when said needle is in said projecting position; and
    biasing means for urging said cover member into said protective position as said needle is withdrawn from the area of flesh to be injected.

13. The injector as claimed in claim 12 further comprising restraining means for restraining said cover member from being moved into said protective position prior to an injection operation.

14. The injector as claimed in claim 13 further comprising activating means for releasing both said releasable spring and said restraining means.

15. The injector as claimed in claim 12 wherein said biasing means comprises a coil spring maintained in a fully compressed state prior to an injection operation.

16. The injector as claimed in claim 15 wherein said coil spring moves to a relatively decompressed state during said injection operation.

17. The injector as claimed in claim 12 further comprising
    manually releasable detent teeth for actuating said automatic injector when released; and
    means for securing said detent teeth in an unreleasable condition and rendering said automatic injector inoperable.

18. An injector as claimed in claim 12 further comprising locking means for locking said cover member in said protective position so as to restrain said cover member against movement which would expose said needle when said needle is in said projecting position.

19. An automatic injector comprising:
    a body having a pierceable membrane at a forward end thereof;

a charge of medicament contained in said body;
a needle held in a sheathed position within said body;
releasable drive means for (1) driving said needle from said sheathed position to an unsheathed, projecting position while piercing said pierceable membrane, and (2) forcing said medicament through said needle;
a cover member being moveable with respect to said body and having a protective position in which it covers said needle when said needle is in said projecting position; and
biasing means for urging said cover member into said protective position to cover said needle when said needle is in said unsheathed, projecting position.

20. An automatic injector comprising:
a body;
a charge of medicament contained in said body;
a needle moveable from a sheathed position within said body to an unsheathed, projecting position from said body;
a graspable rear end cap capable of being grasped by the palm and fingers of a user during an injection operation, said end cap being capable of movement relative to said body;
a slidably moveable cover member for covering said needle when said needle is in said projecting position in which said needle projects from said body; and
a releasable drive assembly which, when released, (1) drives said needle from said sheathed position to said unsheathed, projecting position in which said needle projects from said body and (2) discharges said medicament through said needle, said releasable drive assembly being released in response to said relative movement between said body and said end cap, said relative movement being accomplished during an actuating procedure in which the user grasps the end cap and forces the cover member against a surface to be injected so that said cover member is urged against said body to move said body relative to said end cap and release said releasable drive assembly.

21. The injector as claimed in claim 1 further comprising a membrane for covering said opening in said cover member prior to said injection operation, said membrane being pierced by said needle when said needle is driven from said sheathed position to said unsheathed projecting position.

* * * * *